(12) United States Patent
Evans et al.

(10) Patent No.: US 7,049,348 B2
(45) Date of Patent: May 23, 2006

(54) RESORBABLE STRUCTURE FOR TREATING AND HEALING OF TISSUE DEFECTS

(75) Inventors: Douglas G Evans, Downingtown, PA (US); Jeffrey C Kelly, Wilmington, DE (US); Todd M DeWitt, Pottstown, PA (US)

(73) Assignee: Kensey Nash Corporation, Exton, PA (US)

( * ) Notice: Subject to any disclaimer, the term of this patent is extended or adjusted under 35 U.S.C. 154(b) by 118 days.

(21) Appl. No.: 10/222,593

(22) Filed: Aug. 15, 2002

(65) Prior Publication Data

US 2004/0010048 A1 Jan. 15, 2004

Related U.S. Application Data

(63) Continuation of application No. 10/190,249, filed on Jul. 6, 2002.

(51) Int. Cl.
*C08J 9/00* (2006.01)

(52) U.S. Cl. .......................... 521/82; 521/97; 521/182; 424/426

(58) Field of Classification Search .................. 521/64, 521/61, 97, 182, 82; 424/426
See application file for complete search history.

(56) References Cited

U.S. PATENT DOCUMENTS

| 4,199,864 A | 4/1980 | Ashman |
| 4,636,526 A | 1/1987 | Dorman et al. |
| 5,133,755 A | 7/1992 | Brekke |
| 5,766,618 A | 6/1998 | Laurencin et al. |
| 6,007,580 A | 12/1999 | Tormala et al. |
| 6,169,122 B1 | 1/2001 | Blizard et al. |
| 6,231,942 B1 | 5/2001 | Blizard et al. |
| 6,306,424 B1 | 10/2001 | Vyakarnam et al. |

FOREIGN PATENT DOCUMENTS

| EP | 1 216 717 | 6/2002 |
| WO | WO 91 09079 | 6/1991 |
| WO | WO 02 00275 | 1/2002 |
| WO | WO 02 19947 | 3/2002 |

OTHER PUBLICATIONS

Mooney et al., "Novel Approach to Fabricate Porous Sponges of Poly(D,L-Lactic-co-glycolic acid) Without the Use of Organic Solvents", Biomaterials, 1996, vol. 17, pp. 1417-1422.*

Mooney D J, Novel Approach to Fabricate Porous Sponges of Poly( . . . acid) Without the Use of Organic Solvents, Biomaterials, Elsevier Science Publishers, Jul. 1, 1996, p. 1417-1422.

Hutmacher DW, Scaffolds in Tissue Engineering Bone and Cartilage, Biomaterials, Elsevier Science Publishers, Dec. 15, 2000, p. 2529-2543.

David Pierick and Kai Jacobsen, "Injection Molding Innovation: The Microcellular Foam Process," Plastics Engineering, May 2001, pp. 46-51.

Pfannschmidt, et al., "Production of Drug-Releasing Resorbable Polymer Stents with Foam Structure," Medial Plastics Technology News, Fall 1999-Winter 1999-2000, p. 10-12.

\* cited by examiner

*Primary Examiner*—Irina S. Zemel
(74) *Attorney, Agent, or Firm*—Jeffrey R. Ramberg (57) ABSTRACT

Devices and processes (e.g., improved Plasticized Melt Flow processes (PMF) or improved Phase Separation Polymer Concentration (PSPC), etc.) used to make resorbable and non-resorbable structures for treating and/or healing of tissue defects are disclosed. Among the advantages of using these improved processes are the preservation of molecular weight and the broadening of the processing conditions for temperature sensitive polymers and therapies This reduction in processing temperature, pressure and time can help to preserve the molecular weight and/or integrity of the final product or any additive incorporated therein. The present invention relates to an improved porous implant wherein the pores of the implant present a second modeling material on their surfaces. This second material provides a textured or roughened face to the internal surfaces of pores. Additionally, this second material can be incorporated in sufficient quantity to, among other things, create a microporous network connecting interior closed cell pores with the exterior of the device.

10 Claims, 6 Drawing Sheets

RESORBABLE STRUCTURE FOR TREATING AND HEALING OF TISSUE DEFECTS

RELATED APPLICATION

This application is a Continuation of U.S. patent application Ser. No. 10/190,249, filed on Jul. 6, 2002, entitled Resorbable Structure for Treating and Healing of Tissue Defects.

BACKGROUND OF THE INVENTION

Tissue defects are sometimes repaired with porous scaffolds comprising biocompatible materials. The porous nature of the devices allows the inward migration of cells, followed by the in-growth of tissue, thereby repairing the defect. The pore structure must be controlled to ensure optimal inward cell migration (e.g., sized large enough to accommodate cells, and avoid altering the cell phenotype), from which the new tissue may form. Current devices do not adequately control pore geometry, size, and distribution, with processes that are economically attractive. Additionally, open porous networks facilitate cell migration throughout the implant, thereby speeding up regeneration. Also, mechanical properties of existing porous structures are less than desirable for applications where the implant is subjected to post implant stresses. The porous nature also minimizes the amount of foreign material placed into the patient.

Most processes for producing porous biomaterial implants utilize a leaching method wherein a leachable substance such as sodium chloride is mixed with a biomaterial such as polymethylmethacrylate (PMMA) and later removed with a solvent such as water. U.S. Pat. No. 4,199,864 (Ashman), U.S. Pat. No. 4,636,526, (Dorman et al), and U.S. Pat. No. 5,766,618 (Laurencin et al), describe such methods. Such leaching methods are time consuming and in many instances only a portion of the leachable substance is effectively removed from the implant.

Other processes for creating porous medical implants utilize a vacuum freezing operation as described in U.S. Pat. No. 6,306,424 (Vyakarnam, et al), U.S. Pat. No. 5,766,618 (Laurencin et al), and U.S. Pat. No. 5,133,755 (Brekke). These processes are not generally suited to mass production and often utilize non-biocompatable solvents.

A "plasticized melt-flow" process (PMF) has been developed, in an effort to increase the strength, and reduce costs, of molded polymeric parts. Such a process is described in U.S. Pat. No. 6,169,122 (Blizard et al) and U.S. Pat. No. 6,231,942 (Blizard et al) and by David Pierick and Kai Jacobsen, "Injection Molding Innovation: The Microcellular Foam Process," Plastics Engineering, May 2001, pp 46–51 (such disclosures being incorporated herein by reference). In general, such a process uses a gas (e.g., $N_2$, or $CO_2$) under high pressures to create a supercritical fluid (SCF). The SCF, when depressurized, liberates the gas, thereby creating a porous structure.

The pores in the PMF processes noted above are nucleated by nucleating agents which are added in the range of 2 to 7 percent. As a result the pores may be more homogeneously dispersed through the molded part, than pores seen in other processing methods known in the art. The Pierick-Jacobsen paper reports that the aim of this technology is reducing costs, through the reduction of polymer used and decreasing cycle time, i.e., nucleating agent takes the place of matrix polymer, thereby reducing the amount of polymer needed.

The process is proposed for use in various industrial components (e.g., car mirror housings, ink and Laserjet printer parts), no medical applications, procedures, or devices are disclosed.

A CESP process (Controlled Expansion of Saturated Polymers), however, has been contemplated for use in manufacturing implantable polymer structures by Pfannschmidt, et al, "Production of Drug-Releasing Resorbable Polymer Stents with Foam Structure", Medical Plastics Technology News, Fall 1999-Winter 1999–2000, pp 10–12. The focus of the paper is the use of CESP for the incorporation of "thermally sensitive additives." These additives are suggested to include proteins and growth factors. The devices proposed to deliver these additives are stents. No structural or load-bearing applications are disclosed. In fact, the focus of the invention is the low temperature processability of the invention, however, the resulting process is not readily mass producible.

The CESP may be useful for the delivery of those agents because of the low temperature employed in the CESP process; that is, as previously mentioned, the temperature is not raised to create flow, but rather the pressure is. Therefore, additives may be used that would not survive the temperature of traditional high-temperature molding techniques. However, the CESP process additionally does not adequately address the problem of satisfactory tissue ingrowth or regeneration.

The need for higher strengths in porous polymers has previously been recognized, as in U.S. Pat. No. 6,169,122 (Blizard, et al), where the process is controlled to minimize the cell (i.e., porosity) growth. The aim of the invention is to create homogeneously distributed pores, of a small size (i.e., preferably below 50 microns). To this end, nucleation aids (e.g., talc and titania) are added to the polymer, in an effort to nucleate a larger number of pores during the decompression step (as previously described). However, this paper does not contemplate the problem of satisfactory tissue ingrowth or regeneration, since it strives to create pores that may not be of suitable size to cause effective cellular differentiation and reproduction.

These approaches to utilizing PMF and CESP types of processes for creating porous polymers, for the repair of tissue, would fall short of what is needed in existing surgical procedures. Higher strengths are paramount for implants that may need to withstand any loading following implant; additionally, some implant products (e.g., screws) require continuing strength to withstand the procedural stress. However, proper cell migration into the implant structure, in most cases, require pores on the order of 100 to 250 microns. Therefore, decreasing the pore size below about 100 microns—while increasing strength—could actually prohibit proper cell ingress.

Additionally, talc or titania nucleation aids may not be suited for certain cellular environments, and may further deter cell ingress, or damage or alter normal cellular function and differentiation if such cells were to infiltrate the implant.

The PMF and CESP processes, as disclosed above, creates pores that typically do not communicate with each other. This isolation slows and potentially prevents the continued ingress of cells, through the entire implant cross section, which may delay tissue development, and/or restrict tissue development to the regions at or near the surface of the implant.

Additionally, the closed cell pores of the PMF process do not address the concerns of heterogeneous degradation that occur in massive biodegradable implants. Hydrolysis is not an erosion phenomenon for most biodegradable polymers, but is, instead, a bulk process with random hydrolytic scission of covalent ester bonds. The correlation of in vivo and in vitro rates of hydrolysis has led to the theory that degradation is not facilitated by enzymatic catalysis, or at least not during the initial loss of molecular weight. Hydrolysis is affected by many factors including crystallinity, molecular weight, polydispersity, sterilization process, geometry of the device, total surface area exposed to interstitial fluid, sight of implantation, etc. Although many functions affect biodegradation, hydrolysis has generally been identified to proceed in four main steps i.e., hydration, strength loss, structural integrity loss, and mass loss.

The closed cell pores of the PMF and CESP processes may exasperate problems associated with heterogeneous degradation by providing multiple isolated chambers separated by a thin membrane. These thin membranes may expedite the movement of body fluids deep into the implant where they may pool for a prolonged period of time isolated from interstitial turnover.

In addition, the pores produced by these, and similar, processes typically have uniform or smooth surfaces between the matrix juncture (similar to that of honeycomb structures). Even if these processes were able to yield pores with open architectures, the smooth walls would not be conducive to cell attachment.

Accordingly, there exists a need for homogenous, mass-producible, higher strength, resorbable implants with large pores. The pores may be modeled (i.e., the surfaces made rough or irregular) or intercommunicating and/or foster cell attachment. Embodiments of the current invention address these and other shortcomings in the prior art.

SUMMARY OF THE INVENTION

The present invention provides a resorbable porous structure for healing tissue defects comprising a porous polymer body produced from a process utilizing an SCF but without, in a preferred embodiment, any nucleating aids or fillers.

In yet another embodiment, the present invention relates to an improved porous implant wherein the pores of the implant present a modeling material or agent on their surfaces. This "second" material provides a textured or roughened face to the internal surfaces of pores. Additionally, this second material can be incorporated in sufficient quantity to, among other things, create a microporous network connecting interior closed cell pores with each other as well as the exterior of the device.

In yet another embodiment, the structure is reinforced with a strengthening agent, as will be discussed later.

Certain polymers are very thermally sensitive and extended residence time within melt processing equipment (e.g., PMF equipment) can lead to extensive molecular weight degradation. Other polymers have very narrow processing windows where on the high end of a narrow range the polymer burns and on the low end of the range the polymer does not flow effectively and high stress conditions are created in the final part. By using a gas or solvent to plasticize the polymer, processing temperatures, pressures and time can be reduced. For example, when processing resorbable polymers (e.g. polylactide, polyglycolide, polycaprolactone, etc.), this reduction in processing temperature, pressure and time can help to preserve the molecular weight of the final product. By using described processes for this invention, these polymers can be used for creating large low-stress mass-produced resorbable medical devices.

PMF and PSPC (Phase Separation Polymer Concentration) (as described later) processes may appear complex and varied but in actuality produce similar results. It is recognized that there exists other processes that are known in the art, which also produce analogous systems and results These alternate processes are incorporated herein, to the extent practicable.

In the PMF process, the nucleating agent, if any, can be mixed into a gas permeated plasticized polymer. The gas (e.g. air, oxygen, carbon dioxide, nitrogen, argon, or any inert gas, including combinations thereof) trapped within the polymer begins to expand as the pressure external to the polymer is reduced. As the gas expands it attempts to create uniformly dispersed homogeneous spherical pores. The growth of the pores is disrupted as the walls defining the pores thin to the point that the nucleating agent begins to protrude and therefore the nucleating agent may act as a "modeling agent". As the gas continues to expand the modeling agent particles begin to interfere with each other and/or the expanding pore walls, and force the pore to take on an irregular shape.

In the PSPC process, the modeling agent is dispersed within a polymer solvent solution. The temperature of the mixture is lowered until crystals form within the solution. As the crystals grow they force the polymer into a smaller and smaller area similar to the expanding gas in the PMF process. The growth of the crystals is disrupted as they come in contact with the modeling agent. As the crystals continue to grow they press the modeling agent particles in contact with each other and are thus forced to grow around the particles in an irregular fashion. After solidification vacuum or leaching, a chilled non-solvent removes the solvent crystals.

Figure 1:
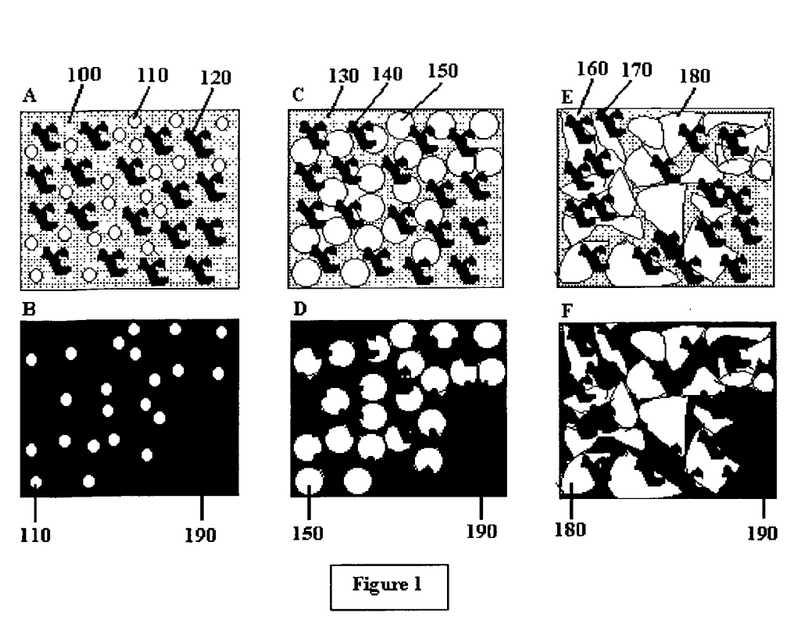
FIG. 1 shows the process by which pores having a textured surface grow into irregular shapes. The drawings focus in on 3 time points in a dynamic process (FIGS. 1A–B, 1C–D, 1E–F).
Figure 2:
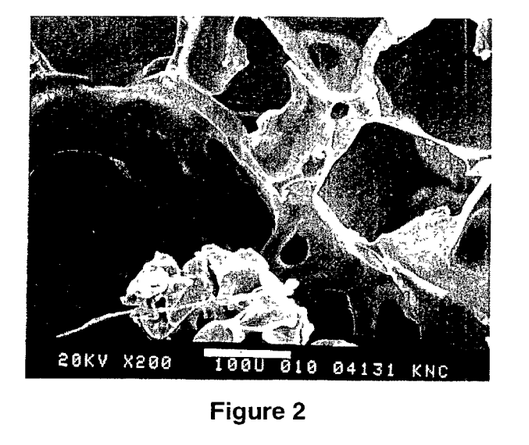
FIGS. 2 and 3 are Scanning Electron Microscope (SEM) images of porous polymer constructs not using a modeling agent, showing a smooth flowing surface, and regularly shaped pores.
Figure 3:
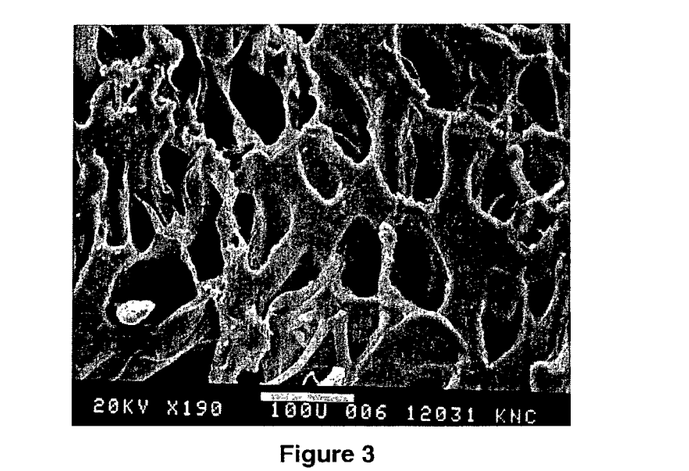
Figure 4:
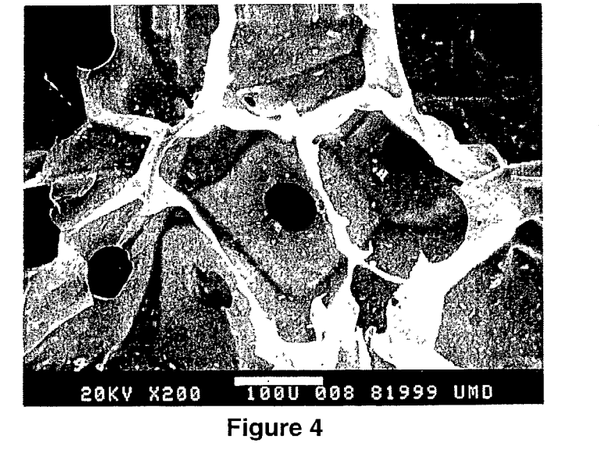
FIG. 4 shows a SEM image of a porous polymer construct using an insufficient quantity of particulate to be classified as a modeling agent showing smooth flowing surfaces and regularly shaped pores.
Figure 5:
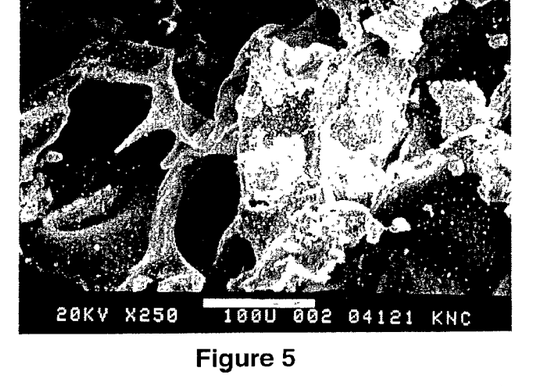
FIG. 5 demonstrates a construct containing approximately the minimal amount of particulate to be considered a modeling agent. Notice the textures surface and weakly irregular pore structure.
Figure 6:
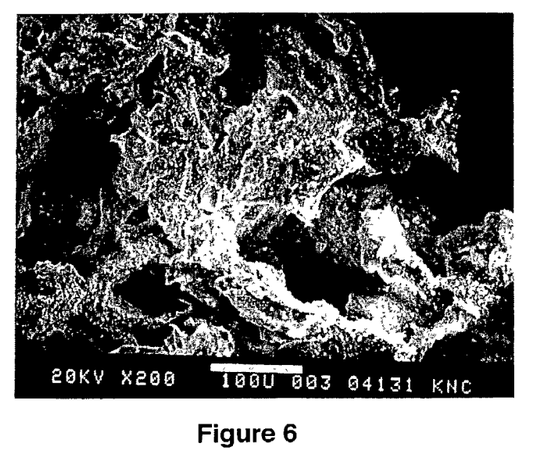
FIGS. 6 and 7 demonstrate constructs containing sufficient quantities of particulate material to be classified as, and have the desired effect of, modeling agents. Notice the highly textured surfaces and large irregular pores resulting from the modeling agents presence.
Figure 7:
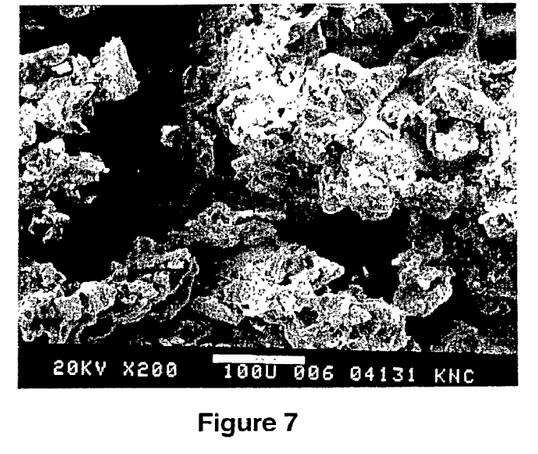
Figure 8:
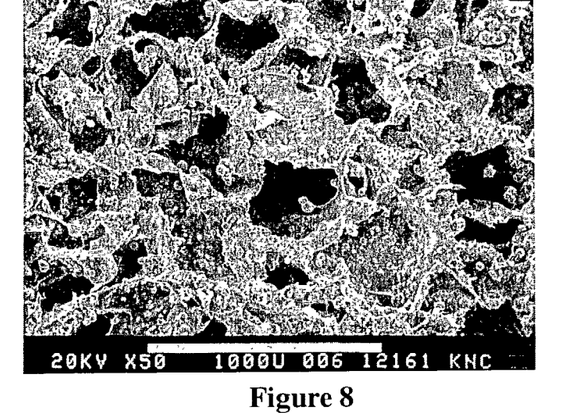
FIGS. 8–10 show constructs demonstrating the use of microspheres as a modeling agent to create irregular pores with a textured surface wherein the modeling agent is embedded into and covered by the polymer.
Figure 9:
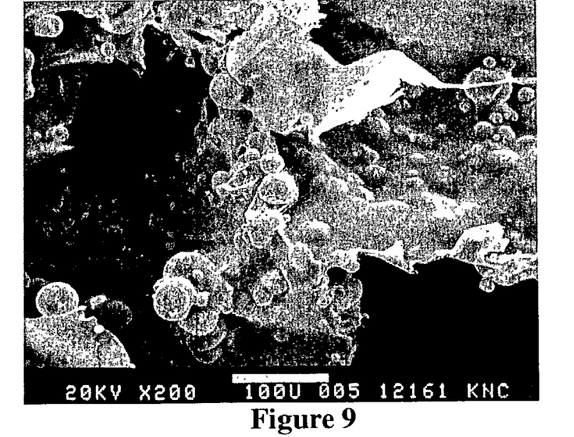
Figure 10:
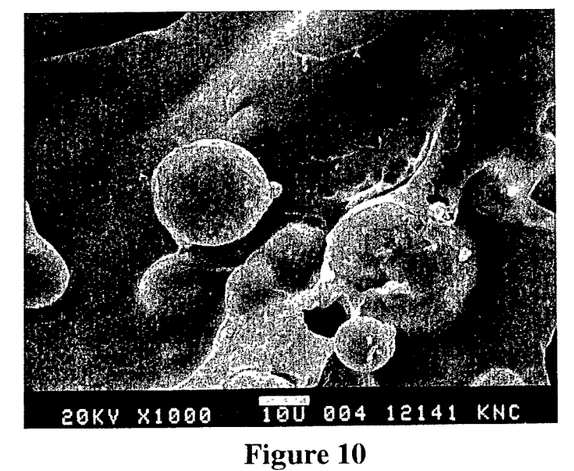
Figure 11:
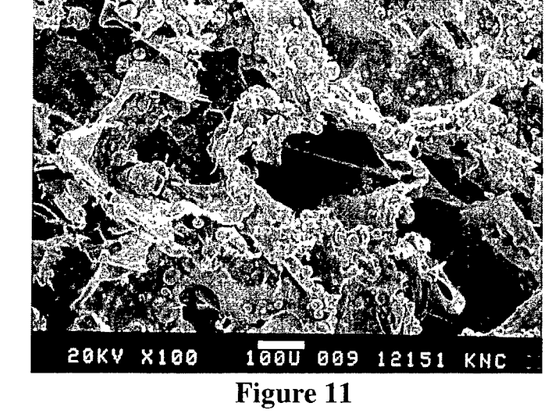
FIGS. 11–13 show constructs demonstrating the use of microspheres as a modeling agent to create irregular pores with a textured surface wherein the modeling agent is held on the surfaces of the pore walls.
Figure 12:
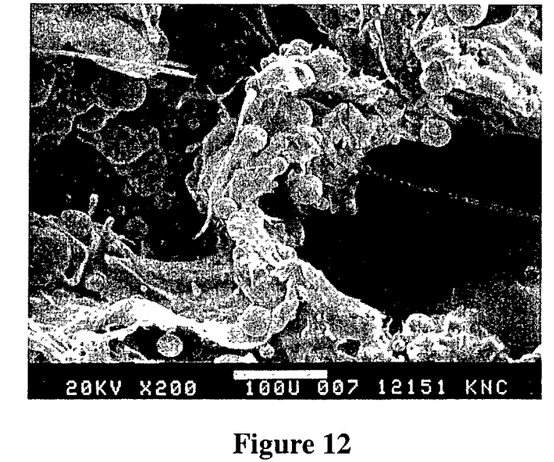
Figure 13:
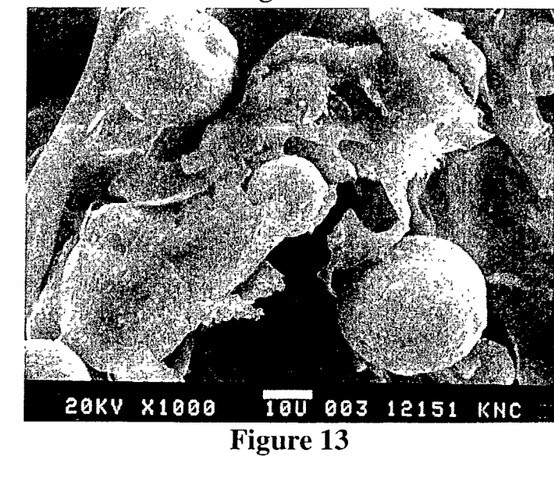

By varying the ratio of polymer to modeling agent in the PMF and PSPC processes, the porosity, pore surface texture and geometry of the matrix may be controlled; wherein matrix is polymer, molding agent and porosity combined. Low polymer constituent concentrations combined with longer processing times allows the growth of large pores, thereby affecting mechanical and physical properties. The rate at which the pores grow (via gas expansion or crystal growth, as appropriate) can determine where in the polymer mass the modeling agent is located. Slow growth of pores allows the modeling agent to migrate within the thinning polymer walls and remain covered or encapsulated (see FIGS. 8–10). Rapid expansion of the pores does not allow sufficient time for the modeling agent to migrate within the walls resulting in partial exposures of the modeling agent (see FIGS. 11–13). The modeling agent may also control physical and biologic properties, as will be described later. Examples of polymers useful for current invention are listed in Table 1.

TABLE 1

Examples and Subtypes of Bioresorbable Polymers for Construction of the Device of the Current Invention:

Alginate
Aliphatic polyesters
Bioglass
Cellulose
Chitin

TABLE 1-continued

Examples and Subtypes of Bioresorbable Polymers for Construction of the Device of the Current Invention:

Collagen

Types 1 to 20
Native fibrous
Soluble
Reconstituted fibrous
Recombinant derived
Copolymers of glycolide
Copolymers of lactide
Elastin
Fibrin
Glycolide/l-lactide copolymers (PGA/PLLA)
Glycolide/trimethylene carbonate copolymers (PGA/TMC)
Glycosaminoglycans
Hydrogel
Lactide/tetramethylglycolide copolymers
Lactide/trimethylene carbonate copolymers
Lactide/ε-caprolactone copolymers
Lactide/σ-valerolactone copolymers
L-lactide/dl-lactide copolymers
Methyl methacrylate-N-vinyl pyrrolidone copolymers
Modified proteins
Nylon-2
PHBA/γ-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β-hydroxypropionate (PHPA)
Poly-β-hydroxybutyrate (PBA)
Poly-σ-valerolactone
Poly-β-alkanoic acids
Poly-β-malic acid (PMLA)
Poly-ε-caprolactone (PCL)
Pseudo-Poly (Amino Acids)
Starch
Trimethylene carbonate (TMC)
Tyrosine based polymers In certain embodiments, the nucleating agent (or modeling agent) may be left out of the processing mix to allow the pores to grow (e.g. since fewer pores are nucleated they may grow larger). Pores in the range of about 50–500 microns may be used in an implant, but may preferably be about 100–300 microns. It is realized that there may be a strength trade-off with this approach.

The modeling agent may also be composed of one or more materials that may have the ability to react with each other to create additional substances within the porosity of the invention. For example, Chitosan and sodium hyaluronate powders can be blended into the polymer and chemically linked to each other within the pores of the invention. This is accomplished by rapid expansion of the pores resulting in exposure of the two modeling agents after which the pores are flooded with a pH-adjusted fluid. The pH-adjusted fluid dissolves the modeling agents within the pores creating a polyelectrolytic system. Within this system chitosan and hylauronate become bound to each other and precipitate out of solution as an insoluble hydrogel.

The incorporation of high modulus strengthening components (e.g., polymers, ceramics or metallics) as the modeling agent will affect the strength and toughness of the resulting structure. The strengthening agent may be in various forms (e.g., particulate, fiber or whisker). The incorporation of these strengthening components improves the strength, such that the pore size may be increased to allow inward cell migration, while retaining or improving the mechanical properties (when compared with a small pore implant without a strengthening component). Additionally, the same modeling agent used to affect the physical properties of the implant can also affect its biologic properties. Hydroxyapatite would not only improve the strength of the implant, but also be capable of, for example, extracting endogenous growth factors from the host tissue bed while functioning as a microporous conduit facilitating movement of interstitial fluid throughout the isolated porosities of the device. Examples of materials useful as modeling agents are listed in Table 2.

TABLE 2

Examples of Materials that may be Utilized as Modeling Agents of the Current Invention:

Alginate
Bone allograft or autograft
Bone Chips
Calcium
Calcium Phosphate
Calcium Sulfate
Ceramics
Chitosan
Cyanoacrylate
Collagen
Dacron
Demineralized bone
Elastin
Fibrin
Gelatin
Glass
Gold
Glycosaminoglycans
Hydrogels
Hydroxy apatite
Hydroxyethyl methacrylate
Hyaluronic Acid
Liposomes
Mesenchymal cells
Microspheres
Natural Polymers
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk TABLE 2-continued Examples of Materials that may be Utilized as Modeling Agents of the Current Invention:

Steel (e.g. Stainless Steel)
Synthetic polymers
Thrombin
Titanium
Tricalcium phosphate The modeling agent can serve multiple purposes which may include but are not limited to:
1. creating a textured surface on the internal surfaces defining the pores;
2. creating a microporous conduit system between pores;
3. reaction-extraction of endogenous growth factors;
4. carrying and/or delivering drugs, biologically active or therapeutic agents;
5. function as a drug, biologically active or therapeutic agent;
6. modifying mechanical properties (e.g. strength, flexibility, etc);
7. function as an in-vivo leachate to increase the overall porosity.

The irregular pore surfaces formed by the modeling agent serves multiple purposes which may include but are not limited to:
1. increased surface area provides greater numbers of anchorage points for cell attachment;
2. increased surface area permits modification to the leaching rate of drugs or other therapeutics;
3. textured surfaces increase quantity of material that can be coated on the interior pore surfaces;
4. irregular surfaces increase the resistance to flow through the implant.
5. engineered surfaces can affect how cells attach, thereby modifying the resulting tissue that is generated.
6. engineered or roughened surfaces can alter the overall pore geometry, which can affect stresses on differentiating cells, thereby dictating cell differentiation modalities.

Additional materials may also be used at the time of manufacture to control the process output (e.g. plastisizers, surfactants, dyes, etc.) For example, processing the polymer with stearic agents will cause the thinning of matrix between the pores, which is most easily penetrable, or rapidly resorbing, following implantation. This will result in a device with high strength, and interconnected pores, which will afford easier migration of cells through the implant.

In yet another embodiment, the polymer and modeling agent, as well as the pores, once formed, can be invested with drugs or other biologically active or therapeutic agents including cells and cellular components (together "therapy") for rapid or slow delivery, as will be discussed. Additionally, microspheres may be incorporated for an additional mode of therapy delivery, as will be discussed. The methods of therapy delivery contemplated by the various embodiments of the current invention include: delivery from the polymer constituent, delivery from the pores, delivery from the modeling agent, and/or delivery via microspheres, including any combination of the preceding modalities. These therapies may treat any underlying condition, which necessitated the implant or procedure, and/or the therapy may treat or support the ingrowing or regenerated tissue. Examples of materials that can be incorporated into and/or delivered by the implant are listed in Table 3.

TABLE 3

Examples with Some Sub-types of Biological, Pharmaceutical, and other Therapies that can be Incorporated into and/or Delivered via the Device in Accordance with the Present Invention Cellular Material Deliverable via this Invention Adipose cells
Blood cells
Bone marrow
Cells with altered receptors or binding sites
Endothelial Cells
Epithelial cells
Fibroblasts
Genetically altered cells
Glycoproteins
Growth factors
Lipids
Liposomes
Macrophages
Mesenchymal stem cells
Progenitor cells
Reticulocytes
Skeletal muscle cells
Smooth muscle cells
Stem cells
Vesicles
Some Sub-types of Biological. Pharmaceutical, and other Therapies Adenovirus with or without genetic material
Angiogenic agents
Angiotensin Converting Enzyme Inhibitors (ACE inhibitors)
Angiotensin II antagonists
Anti-angiogenic agents
Antiarrhythmics Anti-bacterial agents
Antibiotics Erythromycin
Penicillin
Anti-coagulants Heparin
Anti-growth factors
Anti-inflammatory agents Dexamethasone
Aspirin
Hydrocortisone
Antioxidants
Anti-platelet agents Forskolin
Anti-proliferation agents
Anti-rejection agents Rapamycin
Anti-restenosis agents
Antisense
Anti-thrombogenic agents Argatroban
Hirudin
GP IIb/IIIa inhibitors
Anti-virus drugs
Arteriogenesis agents acidic fibroblast growth factor (aFGF)
angiogenin
angiotropin
basic fibroblast growth factor (bFGF)
Bone morphogenic proteins (BMP)
epidermal growth factor (EGF)
fibrin
granulocyte-macrophage colony stimulating factor (GM-CSF)
hepatocyte growth factor (HGF)
HIF-1

TABLE 3-continued

Examples with Some Sub-types of Biological, Pharmaceutical, and other Therapies that can be Incorporated into and/or Delivered via the Device in Accordance with the Present Invention Indian hedgehog (Inh)
insulin growth factor-1 (IGF-1)
interleukin-8 (IL-8)
MAC-1
nicotinamide
platelet-derived endothelial cell growth factor (PD-ECGF)
platelet-derived growth factor (PDGF)
transforming growth factors alpha & beta (TGF-.alpha., TGF-beta.)
tumor necrosis factor alpha (TNF-.alpha.)
vascular endothelial growth factor (VEGF)
vascular permeability factor (VPF)
Bacteria
Beta blocker
Blood clotting factor
Bone morphogenic proteins (BMP)
Calcium channel blockers
Carcinogens
Cells Stem cells
Bone Marrow
Blood cells
Fat Cells
Muscle Cells
Umbilical cord cells
Chemotherapeutic agents Ceramide
Taxol
Cisplatin
Paclitaxel
Cholesterol reducers
Chondroitin
Clopidegrel (e.g., plavix)
Collagen Inhibitors
Colony stimulating factors
Coumadin
Cytokines prostaglandins,
Dentin
Etretinate
Genetic material
Glucosamine
Glycosaminoglycans
GP IIb/IIIa inhibitors L-703,081
Granulocyte-macrophage colony stimulating factor (GM-CSF)
Growth factor antagonists or inhibitors
Growth factors Autologous Growth Factors
B-cell Activating Factor (BAFF)
Bovine derived cytokines
Cartilage Derived Growth Factor (CDGF)
Endothelial Cell Growth Factor (ECGF)
Epidermal growth factor (EGF)
Fibroblast Growth Factors (FGF)
Hepatocyte growth factor (HGF)
Insulin-like Growth Factors (e.g. IGF-I)
Nerve growth factor (NGF)
Platelet Derived Growth Factor (PDGF)
Recombinant NGF (rhNGF)
Tissue necrosis factor (TNF)
Tissue derived cytokines
Transforming growth factors alpha (TGF-alpha)
Transforming growth factors beta (TGF-beta)
Vascular Endothelial Growth Factor (VEGF)
Vascular permeability factor (UPF)
Acidic fibroblast growth factor (aFGF)
Basic fibroblast growth factor (bFGF)
Epidermal growth factor (EGF)
Hepatocyte growth factor (HGF)
Insulin growth factor-1 (IGF-1)
Platelet-derived endothelial cell growth factor (PD-ECGF)

TABLE 3-continued

Examples with Some Sub-types of Biological, Pharmaceutical, and other Therapies that can be Incorporated into and/or Delivered via the Device in Accordance with the Present Invention Tumor necrosis factor alpha (TNF-.alpha.)
Growth hormones
Heparin sulfate proteoglycan
HMC-CoA reductase inhibitors (statins)
Hormones Erythropoietin
Immoxidal
Immunosuppressant agents
inflammatory mediator
Insulin
Interleukins
Interlukins lnterlukin-8 (IL-8)
Lipid lowering agents
Lipo-proteins
Low-molecular weight heparin
Lymphocites
Lysine
MAC-1
Morphogens Bone morphogenic proteins (BMPs)
Nitric oxide (NO)
Nucleotides
Peptides
PR39
Proteins
Prostaglandins
Proteoglycans
Perlecan
Radioactive materials Iodine - 125
Iodine - 131
Iridium - 192
Palladium 103
Radio-pharmaceuticals
Secondary Messengers Ceramide
Signal Transduction Factors
Signaling Proteins
Somatomedins
Statins
Stem Cells
Steroids
Thrombin
Sulfonyl
Thrombin inhibitor
Thrombolytics
Ticlid
Tyrosine kinase Inhibitors ST638
AG-17
Vasodilator Histamine
Forskolin
Nitroglycerin
Vitamins E
C
Yeast The resulting embodiments of this invention will be useful in the improved repair and regeneration of various soft tissue (e.g. tendon, muscle, skin) and hard tissue (e.g. bone, cartilage) types. Furthermore, it is contemplated that organs or sections thereof (e.g., liver, a heart valve, etc., see Table 4) may also be re-grown or regenerated with implants incorporating the technology of this invention.

TABLE 4

Examples of tissues and procedures potentially benefiting from the present invention Ankle reconstruction
Artery
Biopsy
Bone
Bone biopsy
Bone tissue harvest
Burn treatment
Bypass surgery
Cardiac catheterization
Cartilage
Compression fractures
Cosmetic Surgery
Dental
Dura
Elbow reconstruction
Foot reconstruction
Gall bladder
Hand reconstruction
Heart
Heart valve replacement
Hip reconstruction/replacement
Kidney
Knee reconstruction/replacement
Ligament
Liver
Long bone fixation
Lung
Maxillofacial reconstruction/repair
Meniscus
Mosaicplasty
Muscle
Nerves
Osteotomy
Pancreas
Ridge augmentation
Shoulder reconstruction
Skin
Spinal arthrodesis
Spinal fixation/fusion
Tendon
Third molar extraction
Topical wound
Trauma repair
Wrist reconstruction Suitable materials, and additives, for the polymer constituent of these various embodiments includes, but is not limited to, those listed in the above referenced tables. Various resorbable polymers are contemplated by this invention, but components or constituents may also be made of non-resorbable materials, as well. In this regard, In these various embodiments, as well as the balance of the specification and claims, the term "resorbable" is frequently used. There exists some discussion among those skilled in the art, as to the precise meaning and function of resorbable materials (e.g., polymers, ceramics), and how they differ from bioabsorbable, absorbable, bioresorbable, biodegradable, and bioerodable materials. The current disclosure contemplates all of these materials, modalities, or mechanisms, and considers them as equivalent with regard to the function of the current embodiments, even though these processes may be proved to differ significantly in practice, as they are similar in objective and result.

BRIEF DESCRIPTION OF THE DRAWINGS

FIG. 1A shows the genesis of pores 110 in the polymer 100 filled with a modeling agent 120. The pores 110 are the result of expanding gas, vapors, or crystals. FIG. 1B fills in the polymer and modeling agent with a solid black color 190 so that the shape and orientation of the pores 110 can be easily identified. FIG. 1C show the expanding pores 150 coming in contact with modeling agent 140 while pushing polymer 130 out of the way. FIG. 1D fills in the polymer and modeling agent with a solid black color 190 so that the texturing of the pores 150 can be easily identified. In FIG. 1E, the modeling agent particles 170 has been pushed together by the further expanding pores 180. As the modeling agent particles 170 interfere with each other the pores 180 are forced into irregular shapes. The polymer 160 separating the pores has now been squeezed into thin partitions.

DETAILED DESCRIPTION OF THE PREFERRED EMBODIMENTS

An ideal tissue repair/treatment/prosthetic device should possess various of the following properties: (1) it should be chemically biocompatible; (2) it should be partially if not completely resorbable so that the patient's own tissue ultimately replaces at least a portion of the device; (3) it should be porous to allow the infiltration of cells over time; (4) the porosity should provide it with a high surface area to mass ratio for cell attachment and delivery of therapeutics; (5) despite the porosity, it should provide a high degree of structural integrity in order to support, fixate, or treat surrounding tissues until the patient's own bone/tissue heals; (6) the device should have the ability to incorporate additives used to enhance the mechanical or biochemical performance of the device (e.g. strengthening agents, cells, drugs, biomolecules, other agents); and, (7) the device should be mass manufacturable to be able to provide the product at a reasonable price to the consumer. The various embodiments of the current invention address these properties.

The basic PMF process entails four general steps: 1) gas dissolution, 2) nucleation, 3) cell growth, and 4) shaping. During gas dissolution, a blowing agent or supercritical fluid (e.g., $CO_2$ or $N_2$) is injected into molten polymer (together the "chamber material"), in a pressurized process chamber. During nucleation, the gas, which is in solution within the polymer melt, comes out of solution to form a suspension of bubbles within the melt (i.e., acts as a "pore induction fluid"). This occurs as a result of a change in the conditions that affect the solubility of the gas within the polymer melt. For example, a rapid pressure drop or temperature change would affect gas solubility. In some instances, a nucleating agent such as talc is added to the chamber material to promote the formation of a nucleation site. As such, the processing conditions and the presence of a nucleating agent can affect, and therefore lead to control of, the cell growth. The shaping of the final part is controlled by the mold or by some type of final post processing (e.g. machining).

In a preferred embodiment, the improved process of the current invention entails the combining of a system for delivering controlled gas dispersion with a system for producing the porous component in its final form. The component may be produced by one of several methods traditionally used in the manufacture of plastic products. These include injection molding, extrusion, and blow molding.

The gas delivery unit provides a high pressure, accurately metered flow of gas that has reached a stage of Supercritical Flow (SCF). This gas in its SCF state is then delivered to the plastic process equipment at a point in the melt flow of the plastic material that has been determined to produce a final molded or extruded component with an optimized degree of porosity. The addition of a modeling material (as previously described), at this stage or earlier, may result in the formation of irregular pores with a textured surface.

In various of these embodiments, the optimization of this system includes the balancing of three conditions: 1. The gas blowing agent chosen may be introduced in amounts higher than conventionally used in foaming applications and must be completely dissolved in the polymer before pressure is lowered; 2. The blowing agent or SCF gas stays in solution in the melt flow by maintaining a consistent pressure profile; 3. There must be a high rate of change of solubility versus pressure.

The gas delivery system must introduce the proper amount of SCF gas into the melt flow in the plasticising unit of the injection molding or extrusion equipment to create the desired effect on the melt flow. This gas must be introduced at a pressure that is higher than pressure existing in the plasticising unit. In a preferred embodiment, the chamber material may be heated to improve flowablility or to tailor the resulting porosity. Heat may be supplied to the chamber material while it is under pressure in the chamber and/or while it is being expanded in the mold.

Both injection molding and extrusion or blow molding applications of the PMF system should require customization of a standard plasticizing unit to allow creation of a homogeneous and single-phase polymer melt solution, which, in a preferred embodiment, contains a modeling agent. Changes to tooling may be required to optimize production of specific components. In addition, the software that controls machine cycle functions of an injection molding or other processing system may need to be modified.

In yet another embodiment, the process includes subjecting the polymer and any modeling agent to solvent vapors under high pressure. The solvent vapors penetrate and plasticize the polymer without the addition of high heat. The polymer is then rapidly subjected to reduced pressure thereby boiling off the solvent vapors, expanding the polymer and leaving behind a porous structure.

Solvents with low boiling points are favorable in this process (e.g. acetone, tetrahydrofuran, etc.)

In yet another embodiment, the modeling agent is dispersed within a polymer solvent solution. The temperature of the mixture is lowered until crystals form within the solution. As the crystals grow they force the polymer into a smaller and smaller area similar to the expanding gas in the PMF process. The growth of the crystals is disrupted as they come in contact with the modeling agent. As the crystals continue to grow they press the modeling agent particles in contact with each other and are thus forced to grow around the particles in an irregular fashion. After solidification vacuum drying or leaching in a chilled non-solvent removes the solvent crystals.

In addition to catalyzing the formation of irregular shaped pores with a textured surface, a preferred embodiment uses the modeling agent as a strengthening component. The strengthening components are added to the matrix, thereby increasing strength and/or toughness. These strengthening components may be polymers, resorbable or non-resorbable, which may be suitable for primary matrix components themselves (but vary in a mechanical or physical property from the primary polymer); or the strengthening component may be non-polymeric (e.g., ceramic).

There are numerous ceramic systems that display both biocompatability and degradability. One application of devices made with the process of this invention is devices for repair of bone. In the body, the bone itself is the natural storehouse of minerals. The major mineral component of bone is hydroxyapatite, a form of calcium phosphate. Other calcium phosphate salts in bone include monotite, brushite, calcium pyrophosphate, tricalcium phosphate, octocalcium phosphate, and amorphous calcium phosphate. Additionally, bone contains calcium carbonates. Hydroxyapatites and tricalcium phosphates are the most widely studied of the calcium phosphates, which have calcium to phosphate ratios of between 1.5 and 1.67, respectively. Calcium phosphate, $Ca_{10}(PO_4)_6(OH)_2$, is known as a physiologically acceptable biomaterial which is useful as a hard tissue prosthetic. Another calcium mineral used as a bone replacement material is calcium sulfate. Each of these materials either alone or in combination with other materials would serve as suitable strengthening agents. In addition, it is recognized that other osteoinductive, osteoconductive, and inert materials may be suitable for the strengthening agent of the present invention.

Alternatively, strengthening agents may comprise fibers, whiskers, platelets or other oriented additions. These agents also may be resorbable, non-resorbable, or even non-polymeric in composition.

Figure 14:
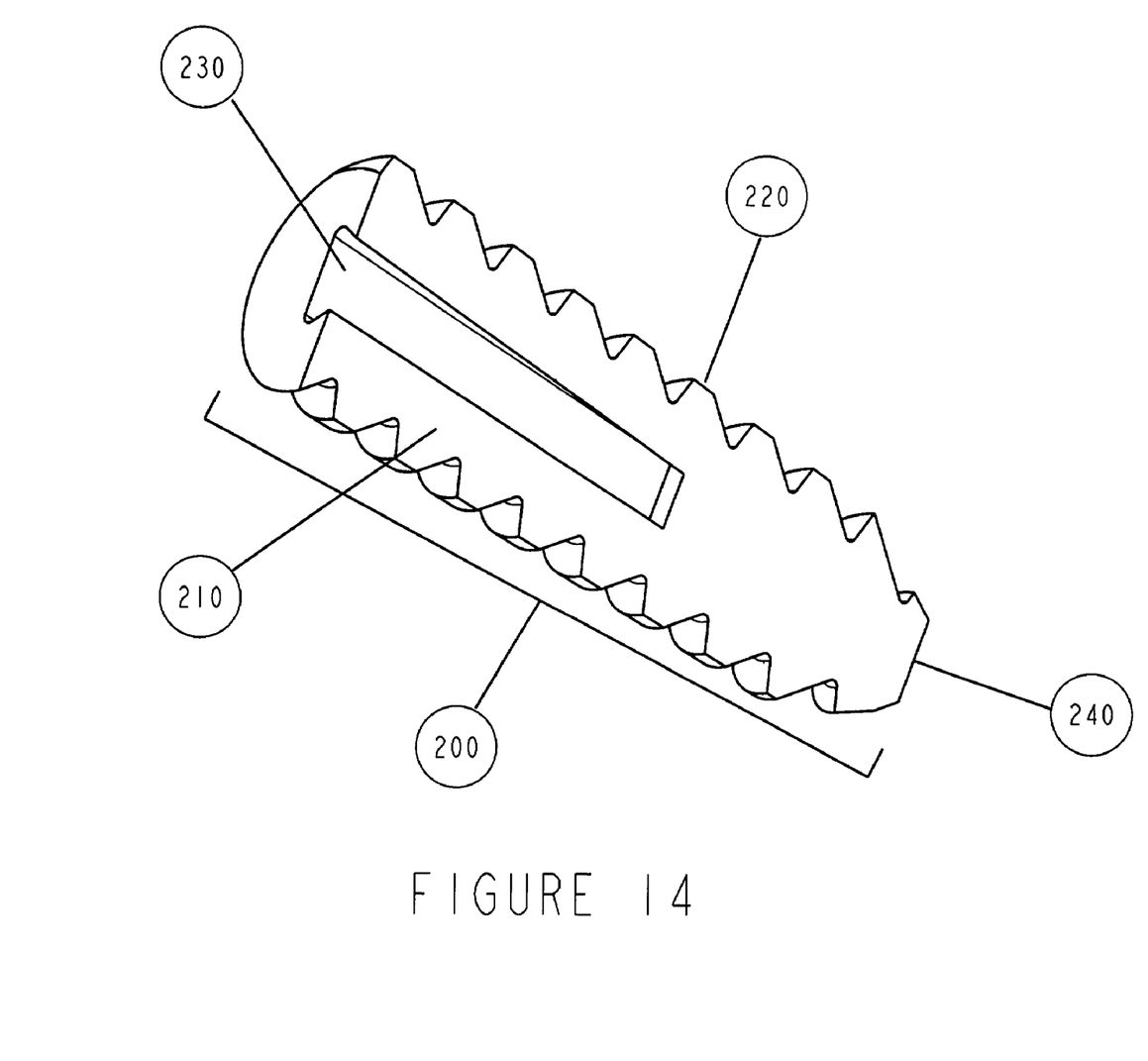
FIG. 14 shows a cross-section of a bone screw, as an example of an application of such a product created by this process.

FIG. 14 shows a cross-section of an implantable screw (e.g. a bone screw) which may be manufactured by the current invention. The typical screw 200 comprises a body 210 with threads 220 or other attachment or securement means (e.g. barbs, etc.), not shown. The screw may have a geometry to accommodate an insertion device, for example a slot 230 or a hexagonal indentation, etc. (not shown) such screw may have a pointed or semi-pointed end 240, or it may be blunt (not shown). Various other fixation and reconstructive devices are contemplated by this invention, including but not limited to fixation plates, rods, pins, rivets, anchors, cages, brackets, etc.

The methods of therapy delivery contemplated by the various embodiments of the current invention include: delivery from the polymer constituent, delivery from the pores, delivery from the modeling agent, delivery from a coating, and/or delivery via microspheres, including any combination of the preceding modalities.

Polymer constituent therapy delivery may be through various mechanisms, including but not limited to, therapy incorporated into the polymer constituent by physical entrapment or by conjugation of the therapy with the monomer or polymer.

Therapy delivery may come from the pores, as release from physical entrapment of the therapy from an enclosed pore, it may come from material adsorbed or loosely adhering to the surface of enclosed or interconnected pores, or it may stay suspended within the pores of the implant awaiting contact with cells entering the pores.

It is recognized that each of the delivery modes could result in different delivery rates. That is, therapy may evolve more rapidly from interconnected pores, than from isolated pores, which may in-turn release therapy faster than any therapy delivered by the polymer constituent (i.e., as it degrades).

In one embodiment the therapy is co-mingled with the various other constituents and components prior to the processing. This allows for some concentration of the therapy to remain in the polymer constituent, while some of the same therapy migrates or precipitates into the porous region of the matrix. An equilibrium phase diagram for the components and constituents would allow the tailoring of the concentration of therapy in each region (i.e., pore or polymer constituent), additionally, therapies with low solubility in either component will aid preferential placement of therapy. Therapy composition, PMF process pressure-temperature parameters, and time, among other variables, will affect the final location and concentration of the therapy.

Addition of a secondary therapy, or other active or inactive agent, may alter the solubility of a primary therapy in either region, thereby altering primary therapy placement.

Alternatively, a secondary therapy may be added because of its complementary therapeutic effect, or because of its preference to precipitate in an alternate region of the matrix (compared with the primary therapy). Any plurality of therapies are deliverable by these techniques.

The therapies may be of various states (i.e., solid, liquid, gas, plasma, etc.), prior to introduction, into the pore forming process; this may affect their ultimate solubility, and it is recognized that the therapy state in the finished matrix may not be the same as what was added.

In some instances it may be beneficial to utilize multiple gases with the polymer processing system. For example, each specific gas could be utilized to carry one or more therapies. The incorporation of the gas into the polymer solution could be customized to optimize the delivery of the therapy. Multiple gases could also be used to create a multi-phasic system of cell sizes and distribution within the final device.

The subject invention can also incorporate cellular additions. Cellular material may be delivered in combination with, or independent of drug delivery. The cellular material may be present on the inside of the implant, outside of the implant, or incorporated within the implant in a porous construct, or other such embodiment. The cellular material may be added to the implant immediately prior to insertion into the body of the living being or may be grown on the implant in the days or weeks prior to implantation so more mature cells are in place when the device is implanted. If the cells are seeded on the implant several days or weeks prior to implantation, the implant may be placed in an in-vitro setup that simulates the in-vivo environment (e.g., where blood or a blood substitute medium is circulated at appropriate pressure and temperature) to acclimate the cells to the host environment. The cell-seeded implant may be incubated in this in-vitro setup at physiologic conditions for several days prior to implantation within the body. Cell seeding techniques have been developed for a variety of cell types. Examples of cellular material that may be seeded on implant include those listed in Table 3.

It is also conceived that a source of cytokines or growth factors (e.g. platelet-rich plasma, bone marrow cells, etc.), whether synthetic, autologous or allograft in origination, can be delivered with the devices of this invention (e.g. incorporated into the implant or delivered via the delivery system). For example, it is known that one of the first growth factors to initiate the cascade leading to bone regeneration are platelet-derived growth factor (PDGF) and transforming growth factor-beta (TGF-β). Each of these growth factors is derived from the degranulation of platelets at the wound, defect or trauma site. It is believed that increasing the presence of such platelets at the wound or trauma site can increase the rate of healing and proliferation needed to regenerate bone.

The application of platelet-rich plasma (PRP) or other autologous blood components is one way to deliver a highly concentrated dose of autologous platelets. PRP is easily prepared by extracting a small amount of the patient's blood and processing it, for example using gradient density centrifugation, to sequester and concentrate the patient's platelet derived growth factors.

Bone marrow may also be added to the present invention to aid in healing and repair.

It is further contemplated that gene therapy may be delivered via the various embodiments of this device. Gene therapies are currently of two primary types, and are both together hereinafter referred to as "gene therapy" or "engineered cells", however others are anticipated; the primary methodologies and basic understandings are described herein (see also table 3).

First, nucleic acids may be used to alter the metabolic functioning of cells, without altering the cell's genome. This technique does not alter the genomic expressions, but rather the cellular metabolic function or rate of expression (e.g., protein synthesis).

Second, gene expression within the host cell may be altered by the delivery of signal transudation pathway molecules.

In a preferred embodiment, mesenchymal stem cells are harvested from the patient, and infected with vectors; currently, preferred vectors include phages or viri (e.g., retrovirus or adenovirus). This preferred infection will result in a genetically engineered cell, which may be engineered to produce a growth factor (e.g., insulin like growth factor (IGF-1)) or a morphogen (e.g., bone morphogenic protein (BMP-7)), etc. (see also those listed in Table 3). Methods of infection as well as specific vectors are well known to those skilled in the art, and additional ones are anticipated. Following this procedure, the genetically engineered cells are loaded into the implant. Cytokines as described and used herein are considered to include growth factors.

Loading of the cells in this embodiment may be achieved prior to processing, during, or immediately following the implantation procedure. Loading may be achieved by various methods including, but not limited to, the injection of a solution containing said engineered cells into the implant, by combining said cells with said matrix components prior to fabrication, or following fabrication or implant.

The term "microsphere" is used herein to indicate a small additive that is about one to three orders of magnitude smaller (as an approximate relative size) than the implant. The term does not denote any particular shape, it is recognized that perfect spheres are not easily produced. In addition to true spheres, the present invention contemplates elongated spheres and irregularly shaped bodies. "Nanosphere" is used herein to denote particles, whether spherical or irregular, that are several orders of magnitude smaller than microspheres.

Microspheres can be made of a variety of materials such as polymers, silicone and metals. Biodegradable polymers are ideal for use in creating microspheres for use in these embodiments (e.g., see those listed in Table 1). The release of agents from bioresorbable microparticles is dependent upon diffusion through the microsphere polymer, polymer degradation and the microsphere structure. Although most any biocompatible polymer could be adapted for this invention, the preferred material would exhibit in vivo degradation. It is well known that there can be different mechanisms involved in implant degradation like hydrolysis, enzyme-mediated degradation and bulk or surface erosion. These mechanisms can alone or combined influence the host response by determining the amount and character of the degradation product that is released from the implant. The most predominant mechanism of in vivo degradation of synthetic biomedical polymers like polyesters and polyamides is generally considered to be hydrolysis, resulting in ester bond scission and chain disruption. In the extracellular fluids of the living tissue, the accessibility of water to the hydrolysable chemical bonds makes hydrophilic polymers (i.e. polymers that take up significant amounts of water) susceptible to hydrolytic cleavage or bulk erosion. Several variables can influence the mechanism and kinetics of polymer degradation. Material properties like crystallinity, molecular weight, additives, polymer surface morphology, and environmental conditions. As such, to the extent that each of these characteristics can be adjusted or modified, the performance of this invention can be altered.

In a homogeneous embodiment (i.e., monolithic or composite of uniform heterogeneity) of a therapy delivering implant material, the device provides continuous release of the therapy over all or some of the degradation period of the device. In an embodiment incorporating microspheres, the therapy is released at a preferential rate independent of the rate of degradation of the matrix resorption or degradation. In certain applications it may also be necessary to provide a burst release or a delayed release of the active agent. The device may also be designed to deliver more than one agent at differing intervals and dosages, this time-staged delivery also allows for a dwell of non-delivery (i.e., a portion not containing any therapy), thereby allowing alternating delivery of non-compatible therapies. Delivery rates may be affected by the amount of therapeutic material, relative to the amount of resorbing structure, or the rate of the resorption of the structure.

Time-staged delivery may be accomplished via microspheres, in a number of different ways. The concentration of therapeutic agent may vary radially, that is, there may be areas with less agent, or there may be areas with no agent. Additionally, the agent could be varied radially, such that one therapy is delivered prior to a second therapy—this would allow the delivery of non-compatible agents, with the same type of sphere, during the same implant procedure. The spheres could also vary in composition among the spheres, that is, some portion of the sphere population could contain one agent, while the balance may contain one or more alternate agents. These differing spheres may have different delivery rates. Finally, as in the preceding example, there could be different delivery rates, but the agent could be the same, thereby allowing a burst dose followed by a slower maintained dose.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes that come within the meaning and range of equivalency of the claims are intended to be embraced therein.

The invention claimed is:

1. A porous polymeric device, said device being implantable to treat tissue or defects therein; said device comprising a polymer matrix, pores, and at least one modeling agent; wherein said device comprises a plurality of internal surfaces that define a plurality of said pores, wherein at least said pores are arranged substantially homogeneously throughout said device, wherein said pores are of irregular shapes due to interactions with said at least one pore modeling agent during processing, and further wherein substantially each of said internal surfaces has expanded at least partially around an external surface of at least one modeling agent, thereby imparting an inward-directed textured or roughened face to said internal surfaces, and wherein said modeling agent is at least partially exposed to said pores, and further wherein said modeling agent comprises chitosan and sodium hyaluronate that can chemically react with each other upon exposure of said pores to a fluid.

2. The device of claim 1, wherein said modeling agent creates a microporous network.

3. The device of claim 3, wherein, but for said modeling agent, pores interior to an external surface of said device would be closed off from said external surface.

4. The device of claim 1, wherein said modeling agent remains substantially completely encapsulated in polymer material.

5. The device of claim 1, wherein said modeling agent comprises a morphology selected from particulate, fibers, platelets and microspheres.

6. The device of claim 1, wherein said modeling agent creates a microporous conduit system between pores.

7. The device of claim 1, wherein said modeling agent is arranged to carry at least one of a drug, a biologically active agent, and a therapeutic agent.

8. The device of claim 1, wherein said modeling agent modifies at least one mechanical property of said device.

9. The device of claim 1, wherein said modeling agent is arranged to function as an in-vivo leachate to increase overall porosity of said device.

10. The device of claim 1, wherein said pores have a size of at least about 100 microns.

* * * * *